United States Patent
Kühn

(10) Patent No.: US 7,263,169 B2
(45) Date of Patent: Aug. 28, 2007

(54) X-RAY COMPUTED TOMOGRAPHY APPARATUS WITH BEAM-GATING DIAPHRAGM

(75) Inventor: Ulrich Kühn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 171 days.

(21) Appl. No.: 11/140,828

(22) Filed: May 31, 2005

(65) Prior Publication Data
US 2006/0115038 A1    Jun. 1, 2006

(30) Foreign Application Priority Data
Dec. 1, 2004   (DE) ..................... 10 2004 058 007

(51) Int. Cl.
*G21K 1/04*   (2006.01)
*G01N 23/083*   (2006.01)

(52) U.S. Cl. .......................................... 378/150; 378/4

(58) Field of Classification Search ............... 378/4, 378/150
See application file for complete search history.

(56) References Cited

U.S. PATENT DOCUMENTS

| | | | | |
|---|---|---|---|---|
| 2,798,958 A | * | 7/1957 | Hudson et al. | 378/39 |
| 4,277,684 A | * | 7/1981 | Carson | 378/7 |
| 4,466,112 A | * | 8/1984 | Covic et al. | 378/7 |
| 5,406,611 A | * | 4/1995 | Schobert et al. | 378/152 |
| 5,493,599 A | * | 2/1996 | Mattson | 378/147 |
| 6,445,764 B2 | * | 9/2002 | Gohno et al. | 378/19 |
| 6,449,340 B1 | * | 9/2002 | Tybinkowski et al. | 378/150 |
| 6,711,235 B2 | * | 3/2004 | Galish et al. | 378/147 |
| 6,934,363 B2 | * | 8/2005 | Seufert | 378/160 |

FOREIGN PATENT DOCUMENTS

DE    OS 102 42 920    3/2004

* cited by examiner

*Primary Examiner*—Edward J. Glick
*Assistant Examiner*—Thomas R. Artman
(74) *Attorney, Agent, or Firm*—Schiff Hardin LLP

(57) ABSTRACT

An x-ray computed tomography apparatus has an x-ray source that can be rotated around a system axis and a diaphragm that is disposed downstream from the x-ray source in the ray propagation direction for gating a fan-shaped ray beam that irradiates a subject. The diaphragm has two gating elements in each of which an absorber element is held, clamped on a carrier at two points in a clamping device provided on the carrier.

15 Claims, 4 Drawing Sheets

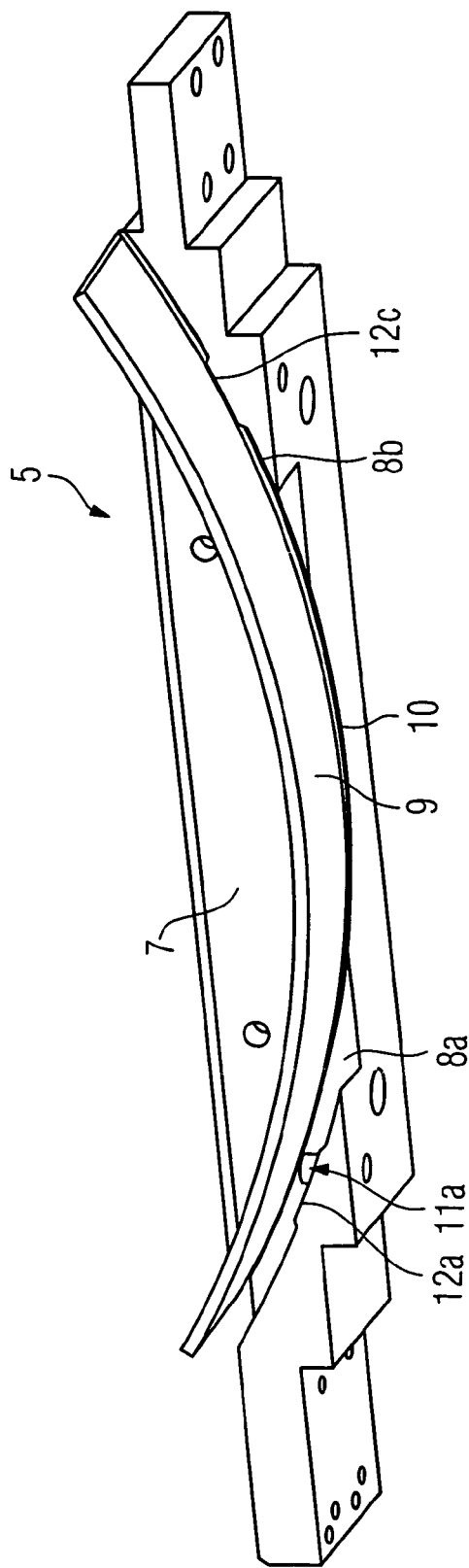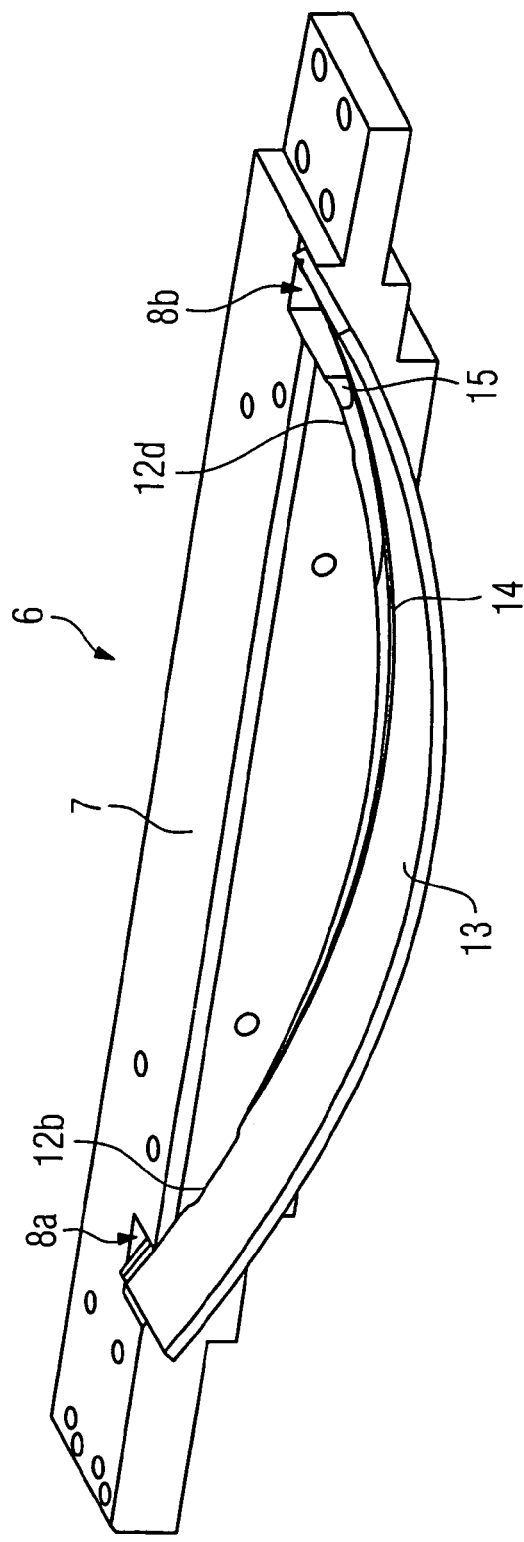

X-RAY COMPUTED TOMOGRAPHY APPARATUS WITH BEAM-GATING DIAPHRAGM

BACKGROUND OF THE INVENTION

1. Field of the Invention

The present invention concerns an x-ray computed tomography apparatus having a beam-gating diaphragm.

2. Description of the Prior Art

An x-ray computed tomography apparatus of the above general type is known from German OS 102 42 920. Curved absorber elements produced, for example, from tungsten or a tungsten composite material are mounted with a positive fit on a carrier manufactured from aluminum in the diaphragm of this known x-ray computed tomography apparatus. Due to the extreme hardness of materials that are composed of tungsten in substantial amounts, a predetermined curvature radius cannot always be produced with the necessary precision in the absorber elements. When mounting the absorber element on the carrier purely by a positive fit, it may occur that the carrier warps in an unexpected manner. This can lead to the absorber element not being able to be positioned with sufficient precision, and thus the geometry of the fan-shaped ray beam, that is set by the diaphragm, to be superimposed on a subject cannot be adjusted with sufficient precision.

SUMMARY OF THE INVENTION

An object of the present invention to provide an x-ray computed tomography apparatus wherein the disadvantages according to the prior art are avoided. In particular an x-ray computer tomograph should be provided in which the fan-shaped ray beam always exhibits an exactly predetermined geometry.

This object is achieved by a computed tomography apparatus having a beam-gating diaphragm wherein the absorber element is clamped at two points in a clamping device provided on the carrier. It is thus ensured in a simple and cost-effective manner that the fan-shaped ray beam always exhibits the predetermined geometry when irradiating the subject. Moreover, production-dependent tolerances of the absorber elements can be compensated.

The term "point", as used herein also encompasses an area that is smaller in relationship to the area of the absorber element. Such an area for clamped attachment of the absorber element is normally at most 30% of the total area of the absorber element facing the ray source.

In an embodiment, the absorber element is fashioned in the form of a curved strip. The absorber element can be produced from a tungsten alloy or a tungsten composite material with a tungsten proportion of at least 91%, preferably 92 to 94%. The absorber element effectively absorbs x-rays and can be produced relatively simply in the design as a curved strip.

The clamping device can have a groove that enables insertion of the absorber element as well as a simple and secure clamping attachment.

The absorber element can preferably is held in the groove by two screws, preferably headless screws. Two projections projecting radially inwardly can be provided on a wall of the groove for connection to the absorber element. The projections serve as supports for the absorber element. They can be disposed approximately opposite a threaded hole accommodating the screws. The absorber element can be forced against the opposite projection by means of the screw. The absorber element is appropriately held on the projection with a positive fit.

In a further embodiment, the absorber element is additionally attached to the projections by means of an adhesive. Such an additional adhesion damps vibrations that may otherwise be conducted by the absorber element.

In a embodiment, projections are provided on the walls of the groove approximately opposite one another. This enables the carrier to accept either an absorber element with a larger radius or an absorber element with a smaller radius. A separation between the opposite walls of the groove appropriately corresponds to more than double the thickness of the strip. This enables the absorber elements to move atop one another, i.e. in an overlapping position, upon closure of the diaphragm. The thickness of the strip is appropriately in the range from 2.0 to 2.5 mm. In the overlapping state, the absorber elements typically exhibit a gap interval of 0.6 to 1.0 mm. As a result, it is appropriate for the distances between the opposite walls of the groove to be in the range from 4.0 to 6.0 mm. The carrier in this case can be fashioned identical in construction for both gating elements. The production expenditure thus can be reduced.

According to a further embodiment, the groove is interrupted so that two groove sections are formed on the carrier. Two projections can be provided approximately opposite one another in each of the groove sections. The carrier can be constructed with a shorter structural height in this embodiment. With such a carrier it is in particular possible to provide a diaphragm with a shorter height. As a result the x-ray computed tomography apparatus can be designed particularly compact.

In a further embodiment, a first absorber element has a first longitudinal groove provided on its convex side and extending parallel to the longitudinal edge. A second absorber element has a second longitudinal groove provided on its concave side extending parallel to the longitudinal edge. Movement of the absorber elements in the direction of the system axis is therewith safely and reliably prevented. The longitudinal grooves can be produced without difficulty before curving the strip.

The inventive clamping attachment of the absorber elements on the carrier ensures a fixed support that also enables a subsequent guiding of the free leading edge of the absorber elements after the mounting of the absorber element.

DESCRIPTION OF THE DRAWINGS

FIG. 3 is a perspective view of a first gating element in accordance with the invention.

FIG. 4 is a perspective view of a second gating element in accordance with the invention.

DESCRIPTION OF THE PREFERRED EMBODIMENTS

Figure 1:
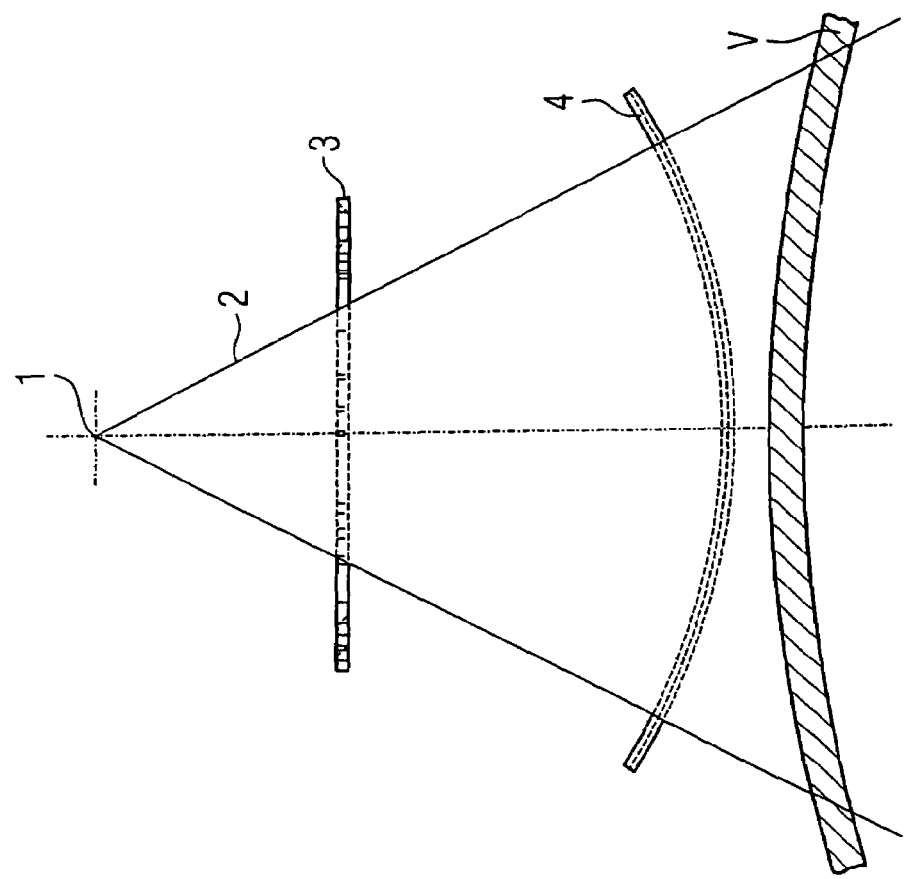
FIG. 1 is a schematic side view of the typical x-ray beam path in an x-ray computed tomography apparatus.
Figure 2:
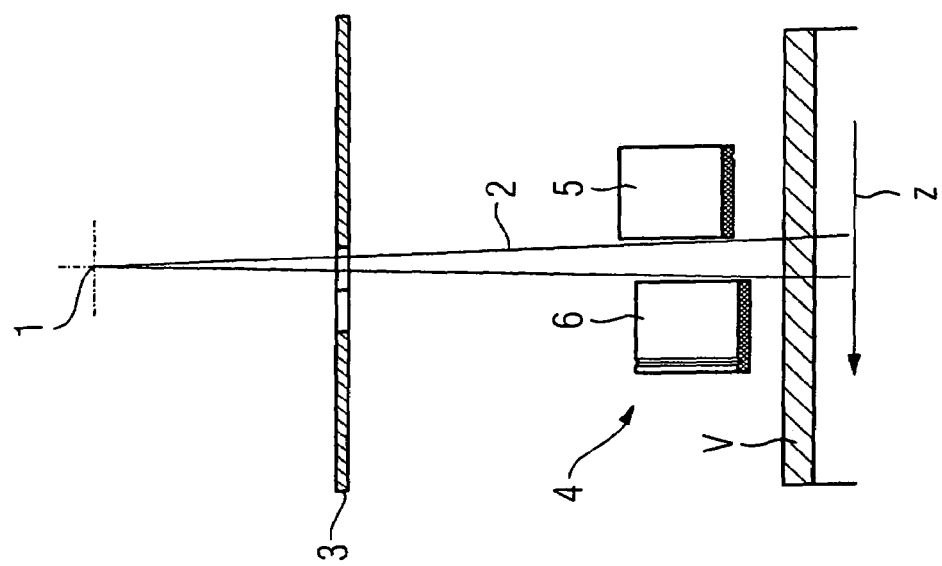
FIG. 2 is a schematic cross-section view according to FIG. 1.

The x-ray beam path of a computed tomography apparatus is schematically shown in FIGS. 1 and 2. The beam emanated from a focus 1 of an x-ray source (not shown). The fan-shaped x-ray beam 2 originating from the focus 1 is defined in terms of its geometry by a pre-diaphragm 3 and a diaphragm 4 arranged downstream in the beam propagation direction. The enclosure of a patient tunnel of the computed tomography apparatus is designated with the reference character V. The diaphragm 4 is formed of a first gating element 5 and a second gating element 6. The first gating element 5 and the second gating element 6 can be moved toward and away from one another parallel to a z-axis shown in FIG. 2.

Figure 7:
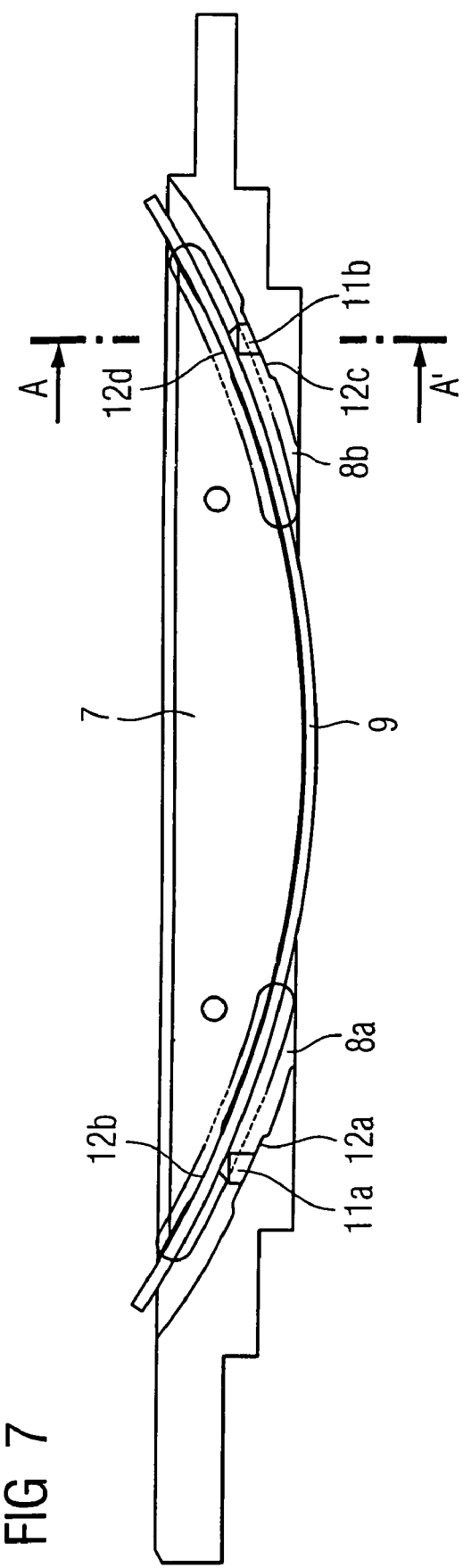
FIG. 7 is a side view of the absorber element according to FIG. 3.

In the first gating element 5 shown in perspective in FIG. 3, a carrier is provided with a first groove segment 8a and a second groove segment 8b. The opposite inner and outer walls of the groove segments 8a and 8b respectively lie on a common circular arc. A first absorber element 9 is accommodated in the groove sections 8a and 8b. The first absorber element 9 exhibits a first longitudinal groove 10 on its convex surface. A first screw 11a provided in the first groove segment 8a engages in the longitudinal groove 10 and presses (forces) the first absorber element 9 against the opposite inner wall of the first groove segment 8a. A second screw 11b with which the first absorber element 9 is pressed against the opposite inner wall of the second grove section 8b is provided in a similar manner (in particular as in the arrangement of FIG. 7) in the second groove segment 8b. The walls of the groove segments 8a, 8b respectively have first, second, third and fourth projections 12a, 12b, 12c, 12d in an approximately opposing arrangement. The first absorber element 9 is pressed against the second and fourth projections 12b, 12d by the screws 11a, 11b. The first absorber element 9 is thus held clamped on the carrier 7 at two points or areas of the second and fourth projections 12b and 12d. In addition to the clamped attachment, a hard-cured adhesive can be provided between the projections 12b, 12d and the first absorber element 9. The adhesive can be formed, for example, from epoxy resin. An additional adhesive connection damps possible vibrations acting on the first absorber element 9.

FIG. 4 shows the second gating element 6 in a perspective view. The carrier 7 of the second gating element 6 is identical with that of the first gating element 5. Like the first absorber element 9, a second absorber element 13 is produced from a curved strip, preferably formed from a tungsten composite material. In contrast to the first absorber element 9, the second absorber element 13 exhibits a larger radius. A second longitudinal groove 14 is provided on the concave side of the second absorber element 13. A third screw (not shown) as well as a fourth screw 15 press the second absorber element 13 against the first projection 12a and the third projection 12c. Similar to the first gating element 5, an adhesive connection can be provided between each of the first projection 12a and the third projection 12c and second absorber element 13. The third and fourth screws 15 engage in the second longitudinal groove 14, similar to the first gating element 5.

Figure 9:
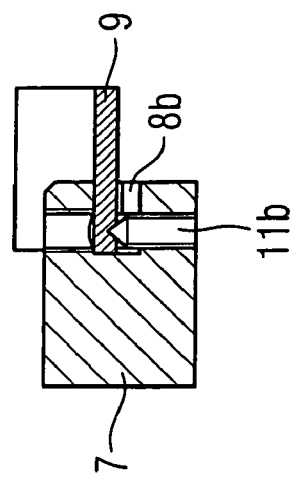
FIG. 9 is a view along section line A-A' in FIG. 7.
Figure 8:
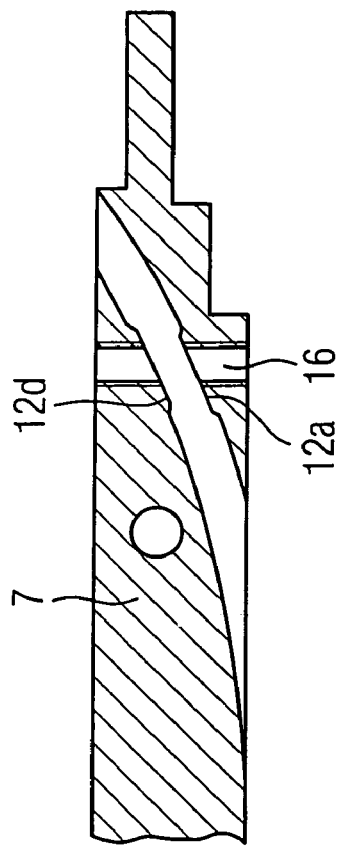
FIG. 8 is a partial cross-section view of the carrier.

As can be seen from FIGS. 8 and 9, the opposing walls of the groove segments 8a, 8b exhibit a separation from one another that corresponds to at least double the thickness of the absorber elements 9, 13. An inner radius of the inner wall of the groove segment 8a, 8b approximately corresponds to the inner radius of the first absorber element 9. An outer radius of the outer wall of the groove segments 8a, 8b approximately corresponds to the outer radius of the second absorber element 13. As is in particular visible from FIG. 8, the opposing projections 12a, 12b, 12c and 12d are penetrated by threaded bores that accept the screws 11a, 11b and 15.

Figures 5, 6:
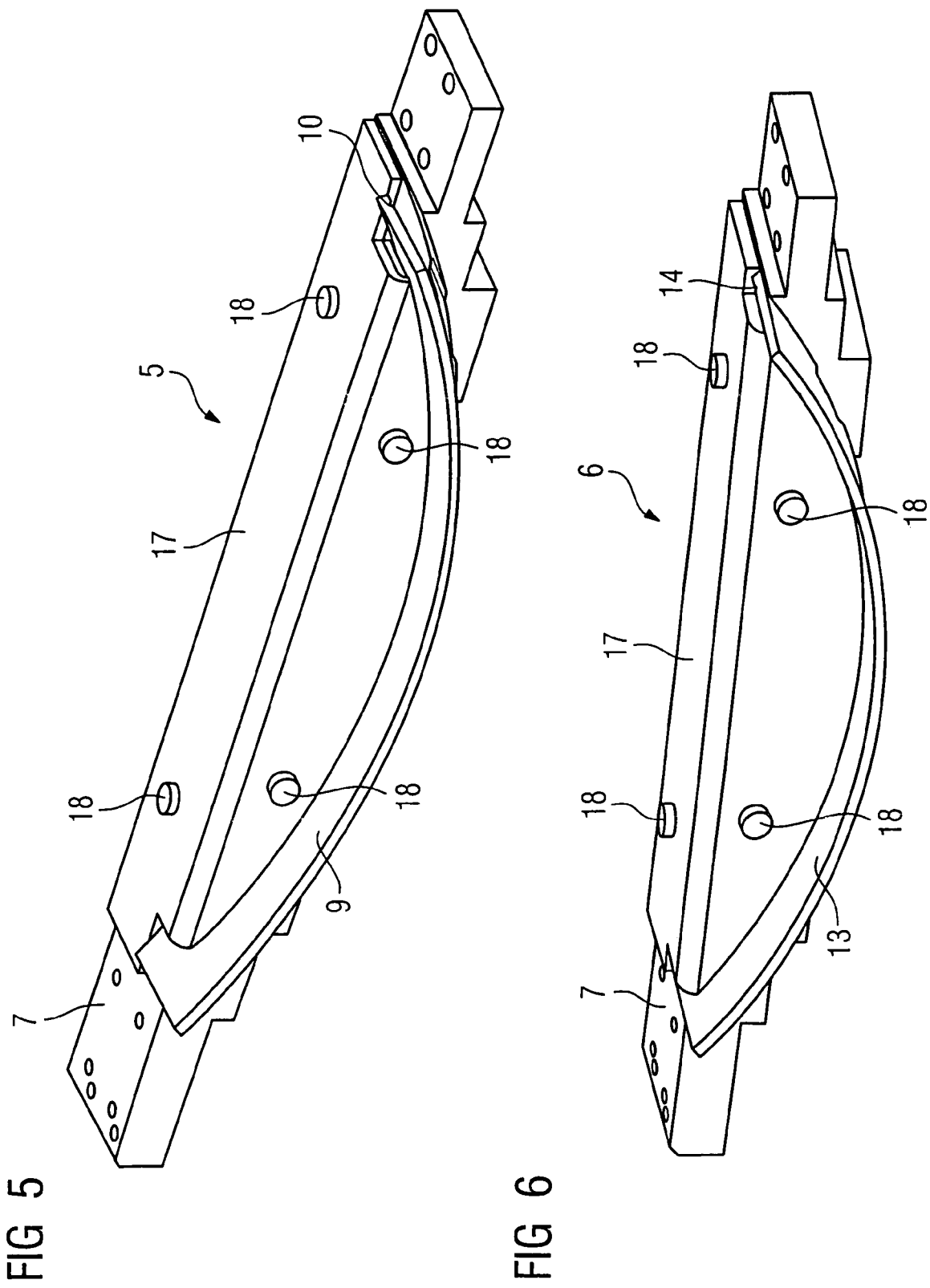
FIG. 5 is a perspective view according to FIG. 3 with lead shielding.
FIG. 6 is a perspective view according to FIG. 4 with lead shielding.

FIGS. 5 and 6 show the first gating element 6 and the second gating element 6, with a lead shielding 17 produced from a lead plate attached to the carrier 7 by lead rivets 18. The lead shielding 17 serves for an improved leakage radiation shielding of a diaphragm box (not shown) that houses the diaphragm 4.

It is particularly advantageous that the same carrier 7 can be used both for production of the first gating element 5 and production of the second gating element 6. Naturally it is also possible in the framework of the invention to provide carriers 7 designed differently. It is not necessary to execute the groove provided for the accommodation of the absorber elements 9, 13 in the form of two separate groove segments 8a, 8b. the groove can also be fashioned continuous. The described embodiment is characterized by a particularly small structural height. In addition, other suitable clamping devices can naturally be provided on the carrier. The absorber elements 9, 13 can be held between two plates braced against one another, or the like.

The carrier 7 is appropriately produced from aluminum. The absorber elements 9, 13 are produced from a tungsten composite material with a tungsten content of 92 to 94%.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray computed tomography apparatus comprising:
a rotary frame rotatable around a system axis;
an x-ray source and a radiation detector mounted opposite each other on said rotary frame, said x-ray source emitting an x-ray beam propagating toward said radiation detector; and
a radiation diaphragm disposed in a path of said x-ray beam for gating said x-ray beam into a fan-shaped beam, having a selectable size, on said radiation detector, said diaphragm comprising movable gating elements, each movable gating element comprising a radiation absorber element having opposite ends defining an absorber element length therebetween substantially perpendicular to said system axis; and a carrier mounted in said diaphragm for movement in a direction along said system axis, and a clamping device that fixedly clamps the absorber element to the carrier at two points spaced from said ends and spaced from each other along said absorber element length.

2. An x-ray computed tomography apparatus as claimed in claim 1 wherein each radiation absorber element is formed as a curved strip.

3. An x-ray computed tomography apparatus as claimed in claim 1 wherein each radiation absorber element is comprised of a material selected from the group consisting of a tungsten alloy containing at least 91% tungsten and a tungsten composite comprising at least 91% tungsten.

4. An x-ray computed tomography apparatus as claimed in claim 1 wherein each radiation absorber element is comprised of a material selected from a group consisting of tungsten alloys containing tungsten in a range between 92% and 94%, and tungsten composites containing tungsten in a range between 92% and 94%.

5. An x-ray computed tomography apparatus as claimed in claim 1 wherein said clamping device comprises a groove in which said radiation absorber element is disposed.

6. An x-ray computed tomography apparatus as claimed in claim 5 comprising two screws penetrating said radiation absorber element at said two points to hold said radiation absorber element in said groove.

7. An x-ray computed tomography apparatus as claimed in claim 5 wherein said groove comprises a groove wall and two projections on said groove wall projecting toward said radiation absorber element at said two points for fastening said absorber element adjacent said groove wall.

8. An x-ray computed tomography apparatus as claimed in claim 7 wherein said carrier comprises two threaded bores respectively disposed opposite said projections, and respectively receiving screws for holding said radiation absorber element in said groove.

9. An x-ray computed tomography apparatus as claimed in claim 7 comprising adhesive between said radiation absorber element and said projections.

10. An x-ray computed tomography apparatus as claimed in claim 7 wherein said projections are disposed on said groove wall substantially symmetrically relative to a center of said groove wall.

11. An x-ray computed tomography apparatus as claimed in claim 5 wherein said groove comprises two separate groove segments.

12. An x-ray computed tomography apparatus as claimed in claim 11 wherein each of said groove segments has a groove segment wall with two projections projecting therefrom to hold said radiation absorber element in the respective groove segments.

13. An x-ray computed tomography apparatus as claimed in claim 5 wherein said groove has a groove thickness that is more than double a thickness of said radiation absorber element.

14. An x-ray computed tomography apparatus as claimed in claim 1 wherein the respective carriers for the respective radiation absorber elements are identical to each other.

15. An x-ray computed tomography apparatus as claimed in claim 1 wherein each radiation absorber element is curved and has a convex side and a longitudinal edge, and a longitudinal groove in said convex side parallel to said longitudinal edge, and wherein said carrier comprises screws engaging said longitudinal groove.

* * * * *